United States Patent [19]

Hughes et al.

[11] 4,381,895
[45] May 3, 1983

[54] METHOD AND APPARATUS FOR AUTOMATIC FLOW-THROUGH DIGITAL REFRACTOMETER

[75] Inventors: Leonard A. Hughes, Oakland; Evan R. Flavell, Albany, both of Calif.; Benjamin C. Willman, Monmouth Beach, N.J.

[73] Assignee: Biovation, Inc., Richmond, Calif.

[21] Appl. No.: 125,549

[22] Filed: Feb. 28, 1980

[51] Int. Cl.³ .......................................... G01N 21/41
[52] U.S. Cl. .................................................. 356/134
[58] Field of Search ........................ 356/128, 130–137, 356/409, 410, 432, 246; 250/577, 573–576

[56] References Cited

U.S. PATENT DOCUMENTS

| | | | |
|---|---|---|---|
| 2,483,102 | 9/1949 | Pierson | 356/134 |
| 3,713,738 | 1/1973 | Bernhardt | 356/128 |
| 3,751,168 | 8/1973 | Llop et al. | 356/136 |
| 4,008,405 | 2/1977 | Neumann et al. | 328/132 |
| 4,193,004 | 3/1980 | Lobdell et al. | 250/577 |

Primary Examiner—Bruce Y. Arnold
Attorney, Agent, or Firm—Owen, Wickersham & Erickson

[57] ABSTRACT

Method and apparatus for determining the concentration of dissolved solids in a sample solution. A refractometer has an enclosing opaque housing, a light source directing a substantially collimated monochromatic light beam through, and a hollow transparent-walled prismatic container adopted for holding a liquid solution to be tested. A light sensor is disposed in the refracted path of the light beam and responds to the exact refraction of the beam caused by passing through the liquid solution. A display is actuated by the light sensor and digitally displays the exact refraction as a function of the concentration of dissolved solids in the liquid sample. Method and apparatus are provided for determining the presence of a sufficient amount of the sample and for automatically commencing the testing in the refractometer.

22 Claims, 9 Drawing Figures

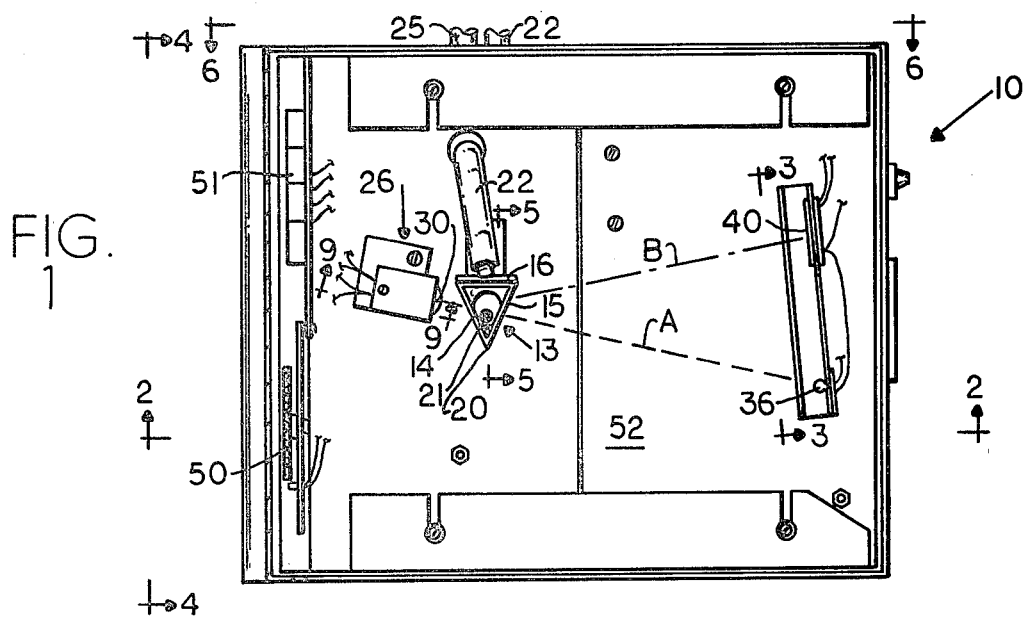
FIG. 1
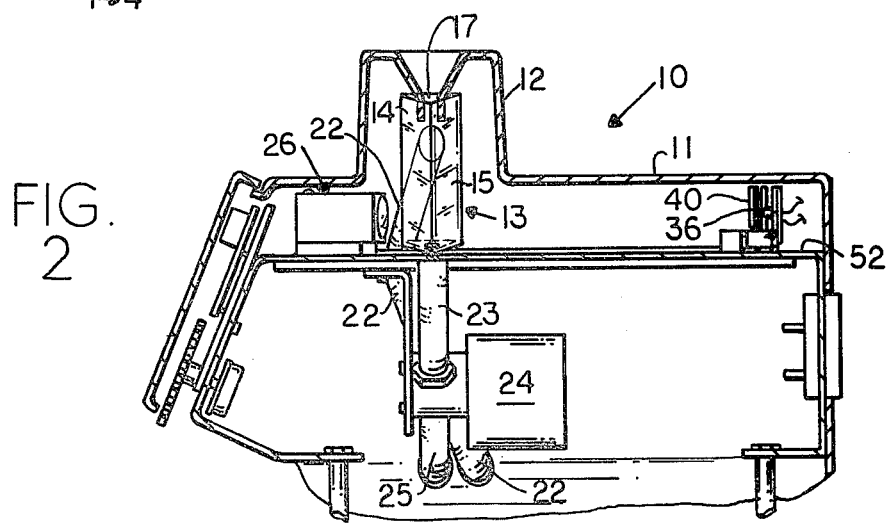
FIG. 2
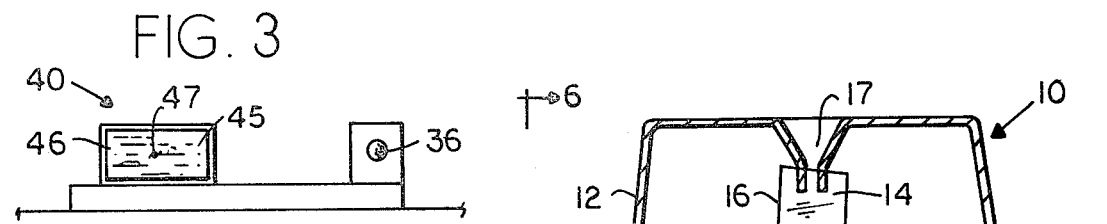
FIG. 3
FIG. 5
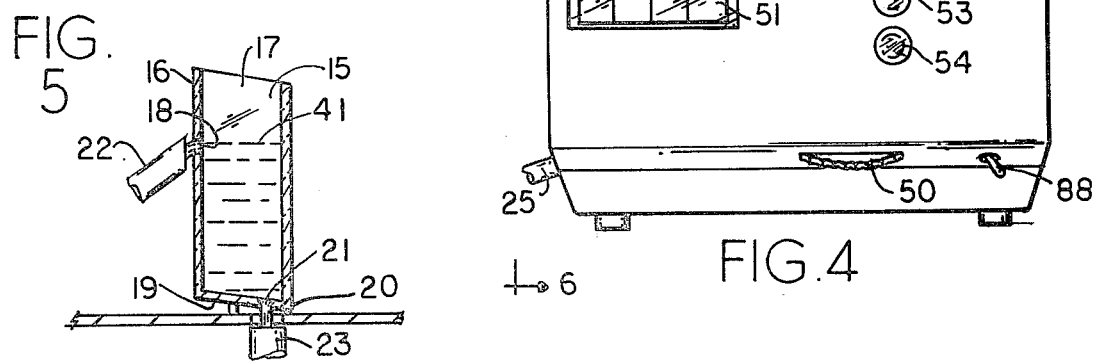
FIG. 4

TO WASTE RECEPTACLE

METHOD AND APPARATUS FOR AUTOMATIC FLOW-THROUGH DIGITAL REFRACTOMETER

BACKGROUND OF THE INVENTION

This invention relates to an improved refractometer and to a method for measuring the light refraction of liquids. As such, the refractometer is adapted for use by individual physicians and others having limited laboratory space.

The method and the device may be used for measuring the concentration of a dissolved solute. For example, the refractometer may be used in clinical testing of biological specimens. More particularly, the refractometer can be used to determine the specific gravity of urine. However, this particular use is an illustrative example, not a limitation, since the device and method of the present application are equally applicable to measuring sugar concentration and other dissolved solids in liquids.

Heretofore, there have been two primary methods for determining the specific gravity of urine. The first method employed a urinometer, a specially calibrated hydrometer. One problem with such hydrometers was that they required a large volume of the specimen, at least 30-40 ml. Moreover, the readings obtained were inherently somewhat inaccurate, due to the formation of a meniscus (or curved top line) along the reading column, the reading being done conventionally from the bottom of the meniscus. Also, since the urinometer readout was on an analog scale, it was therefore subject to operator error.

A second method of determining the specific gravity of urine has employed an American Optical refractometer, a device with the distinct advantage of requiring only two or three drops of specimen. There have been, however, several drawbacks in this device, one being that again, there is an analog readout with its potential operator error. Another drawback has been that the small optical chamber has had to be cleaned between each use: this necessity has added considerably to the time required to perform a series of tests. This prior refractometer has further required both a highpower optical system, a manual visual alignment, i.e., a knob had to be turned by the operator to align two fine lines to obtain a reading, and, again, this increased the potential for operator error.

Among the objects of the present invention is to overcome all of the above drawbacks. Another object is to provide such a device which is no more expensive to manufacture than the American Optical refractometer. Another object is to provide quicker and more accurate determination.

The present invention enables quantitative analysis of various body fluids and other liquids by measuring the displacement of a beam of monochromatic light.

An advantage of the present invention is that the time required to test a given sample is dramatically reduced to the point where up to ten specimens may be tested in one minute.

Another advantage of the present invention is that the possibility of operator error is greatly reduced, since measurement is automatic and the results are displayed digitally, eliminating the need for interpretation of a fine analog scale by the operator.

Another aspect of the digital refractometer of this invention is that erroneous readings caused by the use of too small a sample are eliminated by a novel actuation system which delays the taking of readings until sufficient sample has been used. Further, erroneous readings are prevented by imposing a time delay in taking the reading for a time sufficient to insure that any air bubble in the specimen will have dispersed.

Yet another advantage of the present invention is that only a small amount of specimen is required and no washing between samples is necessary for routine clinical testing.

A further advantage of the digital refractometer of this invention is that no high-power optical system is required, nor is any manual adjustment by the operator required in taking a reading.

SUMMARY OF THE INVENTION

The digital refractometer of the present invention accomplishes the foregoing and other objects by providing (1) a monochromatic substantially point source of light, substantially collimated by a lens, (2) a hollow transparent-walled prism for holding a liquid solution to be studied, (3) a three-terminal photosensor several inches away from the prism which, along with associated electronics, provides a means for measuring the amount of displacement of the light beam due to refraction by the solution in the prism, (4) a second photosensor, and (5) control and display electronics.

The sequence of operation may be as follows:

(1) A sample is poured through a funnel that is integral with the refractometer housing, running down directly into the hollow prism. Any excess sample flows out through an overflow system.

(2) Until the prism chamber is sufficiently filled, the device will not cycle. This is because the light beam is oriented to continue to illuminate a phototransistor until all of the beam is diverted to the measuring photosensor, which is preferably a photopotentiometer. As soon as all of the beam has been diverted from the phototransistor to the displacement photopotentiometer, a first timer is automatically turned on.

(3) The first timer stays on for about 1 to 2 seconds, a sufficient time to enable any air bubbles to leave the prism.

(4) Then, the first timer automatically turns on a sequential second timer for a fixed time, is calibrated to be between approximately 25 and 50 milliseconds for the count cycle. During this time, the amount of refraction is determined, and a digital display actuated.

(5) At the end of its cycle, the second timer triggers a sequential third timer. This third timer opens a solenoid drain valve for approximately two seconds, or long enough for the contents of the prism chamber to drain completely. Due to the novel prism design, sample drainage is complete with only a minimum of carryover. Where extreme accuracy is needed a rinsing system may be added, but this is not necessary for clinical purposes.

(6) The digital display is held until a new sample is poured into the funnel and a new sequence is started, at which time the display is reset to 0.

Additional logic circuitry operates a warning light display so that samples will not be added while liquid is in the prism chamber. A red light may indicate "wait", and a green light may indicate "ready".

The photosensor is grounded at one end, has a plus voltage terminal at the other end, preferably a regulated +5-volt terminal, and a center terminal. The voltage of the center terminal of the photosensor is put into a bridge circuit. Voltage at the center terminal is half the supply voltage when the light beam falls at this exact center of the photopotentiometer. Movement of the spot toward the +5-volt terminal gives increasing voltages, while movement in the other direction gives voltages of less than 2.5 volts. The device is quite linear, so that the voltage put into the bridge circuit is directly proportional to the amount of light refraction.

The bridge output voltage is suitably amplified and is applied continuously to a voltage-to-frequency converter. Thus, the voltage at the center terminal is converted to a digital signal which is passed on to a decade counter, a decoder driver and from there on to display. These components make up an analog-to-digital converter.

Other objects, features and advantages of the invention will become apparent from the following description of an illustrative preferred embodiment.

BRIEF DESCRIPTION OF THE DRAWINGS

In the drawings:

FIG. 1 is a top plan view of an instrument embodying the principles of the invention, with the cover removed;

FIG. 2 is a view in section taken along the line 2—2 of FIG. 1, the bottom portion being broken off to conserve space;

FIG. 3 is an enlarged fragmentary view in section taken along the line 3—3 of FIG. 1, showing the photopotentiometer and phototransistor;

FIG. 4 is a front plan view, partially in section, of the instrument of FIG. 1;

FIG. 5 is an enlarged fragmentary view in section, taken along the line 5—5 of FIG. 1 of the flow-through prism;

DETAILED DESCRIPTION OF THE PREFERRED EMBODIMENTS

Figure 6:
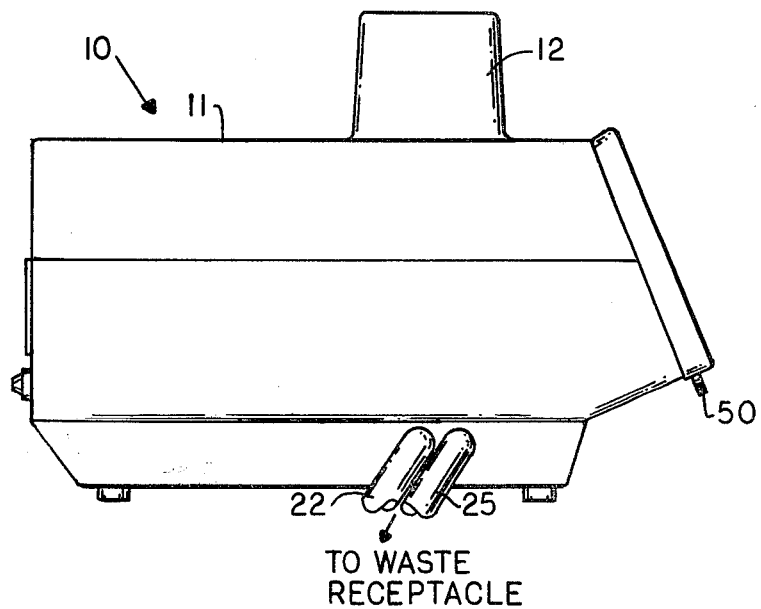
FIG. 6 is a side view taken along the line 6—6 of FIG. 4.

As shown in FIG. 2, a digital refractometer 10 embodying the principles of the invention includes an enclosing opaque upper housing member 11 which, in a preferred embodiment, may be made of a single piece of molded plastic. The opaque housing member 11 may be shaped to provide an integral funnel 12 through which a sample may be poured into a hollow prism 13. In an embodiment not adapted for flow-through capabilities, the hollow prism 13 may be removable and the funnel 12 may be replaced by a hinged or sliding opaque lid providing access to the removable prism when open and blocking light when closed during operation. However, this illustrated embodiment is preferred, and here the prism 13 is secured in a fixed position. Transparent walls 14 and 15 of the prism 13 may be made of any suitable optical material including, for example, glass, plastic, and quartz. The third wall 16 need not be transparent, though it can be.

In the embodiment adapted for flow-through capability, as may be seen in FIGS. 2 and 5, the hollow prism 13 is preferably triangular, having one non-optical side wall 16 and two transparent optical side walls 14 and 15 which meet each other at some suitable angle between about 40° and about 55°, to provide a good spread of light over a range of refractions. The prism 13 has an outlet opening 17 at its top, an overflow opening 18 in its side wall 16 disposed approximately two-thirds the height of the prism 13, a floor 19 sloped downwardly from the side wall 16 towards a point 20 along the edge where the two optical side walls 14 and 15 meet, and a drain opening 21 located at approximately the lowermost point of the sloped floor 19.

The overflow opening 18 is connected to an overflow tube 22, through which excess sample may be conducted (See FIG. 6) to a waste receptacle outside the digital refractometer 10. The drain opening 21 is connected by a drain tube 23 to the inlet side of a solenoid drain valve 24, which remains closed during filling and testing and is then opened automatically to evacuate the hollow prism 13 after the test has been completed. The outlet side of the solenoid drain valve 24 may be connected to the same outside waste receptacle through the drain tube 23 or through a separate waste tube 25.

Figure 7:
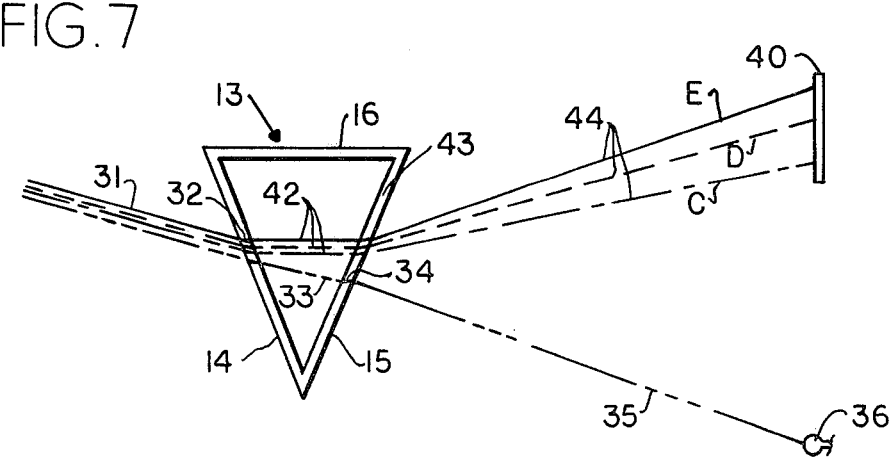
FIG. 7 is a diagrammatic top plan view of the prismatic container showing various light refraction paths.
Figure 8:
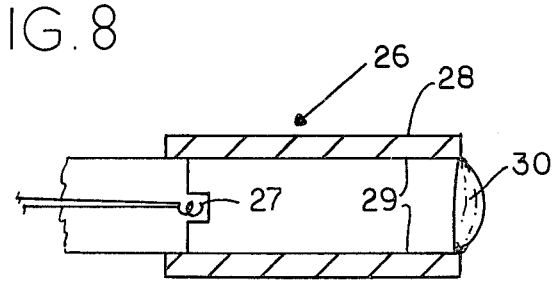
FIG. 8 is an enlarged view in longitudinal section of the light source, taken along the line 8—8 in FIG. 1; the size of the light-emitting diode is exaggerated.

A light source 26 is provided at one side of the prism 13 to direct light toward and through the wall 14. This light source 26, as shown in FIG. 8, preferably comprises a light-emitting diode 27 of a type that produces monochromatic light, housed in a metal member 28 through which is a bore 29 housing a lens 30 on the end opposite the light-emitting diode 27. The diode 27 preferably has a flat square emitting surface about 20 mils square, and thus is substantially a point source of light. The light source 26 must emit a beam of collimated monochromatic light. It may be a laser, an incandescent bulb, an LED, a zirconium arc lamp or the like. The lens 30 acts to substantially collimate the light of the diode 27 and direct it in a beam 31 toward the transparent prism wall 14. As shown in FIG. 7, the wall 14 slightly refracts the beam 31 along prism wall path 32, and then the beam goes across the hollow interior of the prism 13 to the transparent wall 15. When the prism 13 is empty, the beam of light follows the interior path 33 from the wall 14 to the wall 15, is slightly refracted along the prism wall path 34 in the wall 15, and then emerges as a slightly divergent narrow beam 35 directed at a phototransistor 36. FIG. 2 shows that the light source 26, the hollow prism 13, and the phototransistor 36 are disposed in a height relationship such that the beam 35 goes directly to and illuminates the phototransistor 36 when the prism 13 empties.

A photopotentiometer 40 shown in FIGS. 1, 2, and 3 is also disposed at substantially the same height as the phototransistor 36. When there is liquid 41 inside the hollow prism 13 and when the liquid fills the prism 13 all the way up to the overflow opening 18, then, as shown in FIG. 7, the beam 31 follows interior refracted 42 path through the liquid 41 and a path 43 through the prism wall 15, and emerges as a refracted beam 44 directed at the photopoteniometer 40. Unlike the beam 35, which is always directed to the same point, the refracted beam 44 is affected by the solids content in the liquid 41. It may be directed toward the middle of the photopotentiometer 40. If the photopotentiometer 40 is placed across a +5 volts at one end terminal 45 and ground at its other end terminal 46, a beam 44 directed at its middle would give a voltage of 2.5 at the third or center terminal 47. Movement of the beam 44 toward the terminal 45 increases the voltage at the center terminal 47, while movement of the beam 44 toward the terminal 46 decreases the voltage at the center terminal 47. The operation is substantially linear. In a preferred configuration the spot moves about 3.5 mm for specific gravities between 1.000 and 1.040; the voltage change at the center terminal 47 is between about 1.7 volts and 3.3 volts.

FIG. 1 shows the location of control means 50 and display means 51. The relative positions of the light source 26, the hollow prism 13, the photopotentiometer 40, and the phototransistor 36 on a compartment floor 52 are also shown. Line A represents the path of the light beam when the hollow prism 13 is not sufficiently filled with sample, illuminating the phototransistor 36. Line B represents the path of light beam when the hollow prism 13 is sufficiently filled with sample 41, being refracted to illuminate a point along the photopotentiometer 40. The amount of refraction and consequently the point location along the photopotentiometer 40 which is illuminated is a function of the concentration of dissolved solutes in the sample being tested.

More specifically, as shown in FIG. 7, the solids content of the liquid 41 affects the light refraction path B of FIG. 1. Thus, clear water with a specific gravity of 1.000 causes the light to refract along a beam C in FIG. 7. Urine with enough dissolved solids to give a specific gravity of 1.020 causes the light to refract along a beam D, while urine with more dissolved solids, enough to give a specific gravity of 1.040, cause the light to refract along a beam E. Each of the beam C, D, and E strikes the photopotentiometer 40 at a different location and accordingly changes the output voltage at the terminal 47. Specific gravities can then be determined to an accuracy of ±0.001, and the values are almost instantly displayed.

The relative locations of the control means or calibration wheel 50, the display means 51, a green "ready" light 53, and a red "wait" light 54 are shown in FIG. 4.

Figure 9:
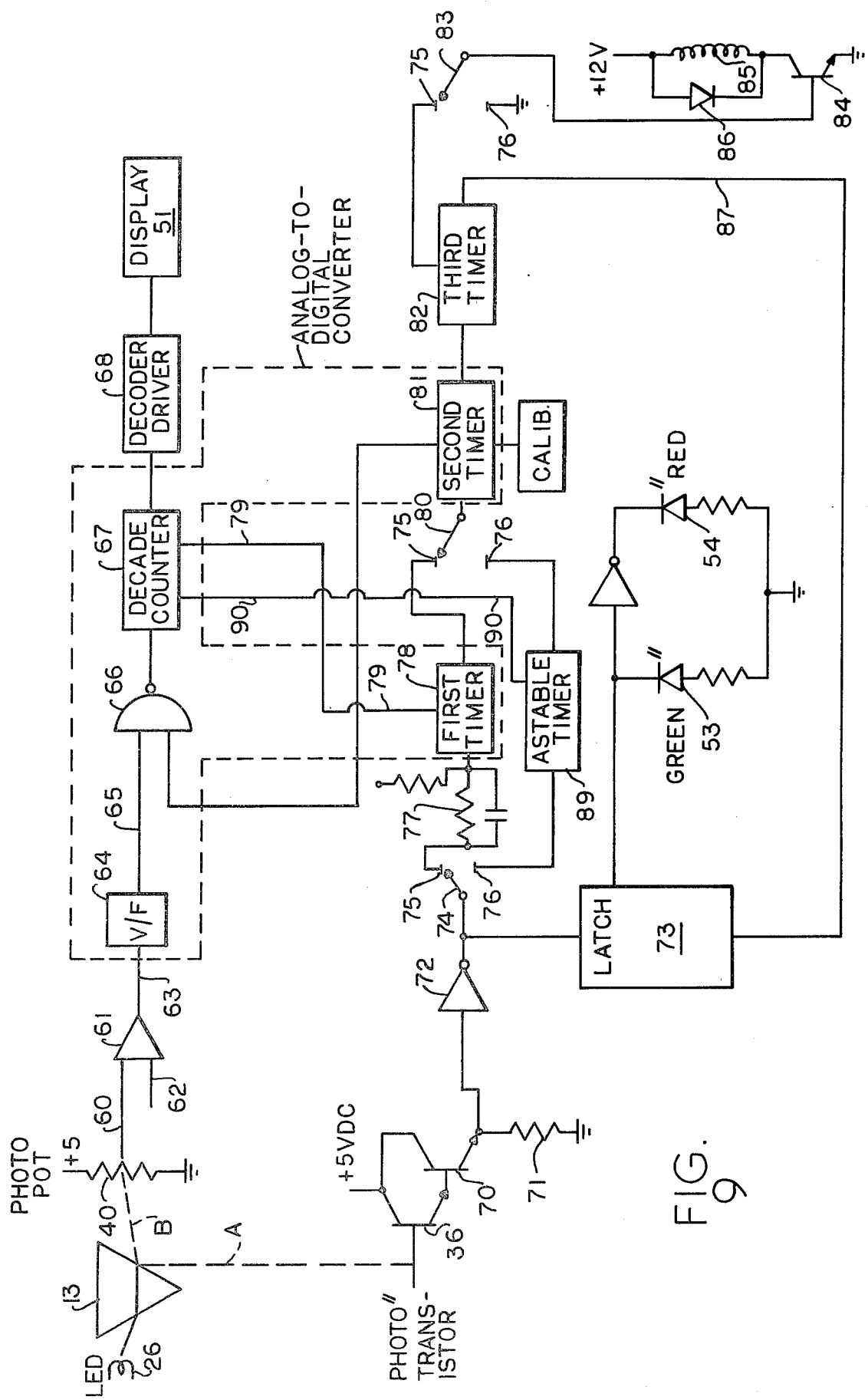
FIG. 9 is an overall block diagram of the circuits included in the digital refractometer of FIG. 1.

FIG. 9 is a circuit diagram showing mostly in block form the way in which elements available from the prior art may be assembled in order to get the desired results. Alternatively, a microprocessor may perform all of the electronic functions except the sensing and amplifying functions. The LED 26 is shown as the light source, and its light after collimation passes through the prism 13, going either by path A to the phototransistor 36 or by path B to the photopotentiometer 40.

When the light from the LED 26 is directed by path B to the photopotentiometer 40 because there is solution in the prism 13, a refracted beam 44 is produced, as has already been described, which depends upon the amount of solids dissolved in the solution 41. A resultant signal then passes by line 60 to a differential amplifier 61 which is also fed by a reference line 62. The amplified difference signal is sent by a lead 63 to a voltage-to-frequency converter 64 which, in turn, produces and transmits a digital signal along lead 65 to a gate 66, preferably a NAND gate. The gate controls the initiation and cessation of a decade counter 67, which is connected through a decoder driver 68 to a display 51.

When the prism 13 is empty, the beam from the LED 26 goes through the prism 13 along path A to the phototransistor 36. A voltage, for example +5 volts DC, is applied to the collector of the phototransistor 36 while the emitter is connected to the base of a second transistor 70, the collector of which is also connected to the +5 DC volts source. The emitter of the second transistor 70 is held above ground by a bias resistor 71 and is sent to a Schmitt trigger 72 which sends a signal to a latch circuit 73 and also to a first switch 74. The switch 74 has a normal operating position 75 and a calibration position 76. When the switch 74 is in its normal operation position 75, as shown in FIG. 9, the signal is coupled by a resistance capacitance network 77 to the trigger input of a first timer 78.

The first timer 78 is connected by a lead 79 to the decade counter 67, and actuation of the first timer 78 resets the counter 67 to zero. Upon completion of its time interval, the first timer 78 sends a signal via a second switch 80 that actuates a second or testing duration timer 81. Actuation of the second timer 81 sends a signal via a line 81a to the NAND gate 66 that opens the gate and starts the decade counter 67 in its counting operation, which operation lasts only for the interval the second timer 81 is set for, and then turns off. When the NAND gate 66 is actuated, the digital signal is transmitted to the decade counter 67, and the decade counter 67 counts the digital pulses generated by the voltage-to-frequency converter 64 and passing through NAND gate 66 for the period of the second timer 81. When the second timer 81 completes its timed interval, the NAND gate 66 is closed, and then the decade counter 67 no longer receives a signal to count. The counted signal goes to the decoder driver 68 and from there to the display 69. It may be seen that the components 64, 66, 67, 68, 78, and 81 comprise an analog-to-digital converter.

When the second timer 81 reaches the end of its interval, it then actuates a third timer 82 to energize a solenoid 85 for the solenoid drain valve 24. There is a diode 86 in parallel with the solenoid 85. The third timer 82 also sends a signal along lead 87 to the latch 73.

The latch 73 controls whether the green light 53 or the red one 54 is lighted. At the end of its period, the third timer 82 causes the latch 73 to light the green light 53, showing that the device is ready to receive the next sample. When another sample has been put into the prism 13, the phototransistor circuit is actuated to send forth a signal from the Schmitt trigger 72 to the latch 73 so that the red light 54 is actuated. It remains actuated until the third timer 82, again, actuates the green light 53.

The calibration mode is selected by control switch handle 88 (as shown in FIG. 4). Other elements in the calibrating circuit (as shown in FIG. 9) include a first switch 74 connected to an astable timer 89, connected to a second switch 80, connected to a second timer 81, connected to a calibrating potentiometer 50, and a third switch 83.

When control switch handle 88 is put in the calibrate position, switches 74, 80, and 83 are moved to their respective calibrate positions 76. When phototransistor 36 ceases being illuminated and the resulting sharp cut-off in the circuit is caused by the Schmitt trigger 72, the astable timer 89 is actuated because the first switch 74 is in calibrate position 76. The astable timer 89 turns on and off in one second pulses causing the decade counter 67 to reset to zero via connection through a lead 90. Since the second switch 80 is in calibrate position 76, the astable timer 89 also re-initiates the second timer 81, which, through its connection via the lead 82 to the NAND gate 66, causes repeated counting periods by the decade counter 67 and therefore repeated displays of the number corresponding to the concentration of dissolved solids in the sample on the display 51 through the decoder driver 68.

The third switch 83, also being in the calibrate position, conducts the output from the third timer 82, (which would normally actuate the solenoid 85 and cause draining) to ground, so that the sample does not drain during calibration.

The potentiometer 50 controls the length of time for which the second timer 81 is set. By testing a standard solution 41, having a known concentration of dissolved solids, in the calibrate mode, the period of the second timer 81 can be adjusted by the calibrating wheel 50 so that the decade counter 67 will count pulses from the analog-to-digital converter 64 for a time which will result in a reading on the display 51 which is the same as the known concentration of the standard.

Once the calibration is completed, the control switch handle 88 may be moved back to the test mode, the refractometer will go through a normal testing sequence commencing at the sharp cutoff by the Schmitt trigger 72 and will drain at the end since the third switch 83 is again passing the signal for the third timer 82 to actuate the solenoid 85 for draining.

The operation sequence will now be described with reference to FIGS. 1, 2, and 9. At the beginning, the green "ready" light 53 is lighted, the hollow prism 13 is empty, the solenoid drain valve 24 is closed, and the phototransistor 36 is illuminated by the beam from the light source 26. A sample 41 is poured through the funnel 12 into the inlet opening 17 of the hollow prism 13, filling the prism 13. Any excess sample, which could lie above the overflow opening 18 goes to waste via the overflow tube 22. Once the hollow prism 13 is filled sufficiently for testing, the light beam will be refracted away from the phototransistor 36, cutting off its output. This circuit is amplified and the Schmitt trigger 72 makes a sharp cutoff in the electronic circuit. This sharp cutoff actuates the first timer 78, and also actuates the latch 73 to turn off the green "ready" light 53, and to turn on the red "wait" light 54.

The first timer 78 measures a period of approximately 1 to 2 seconds, a sufficient time to allow any air bubbles in the sample to disperse. The first timer 78 then actuates the second timer 81 and resets the decade counter 67 to zero.

In the meantime, the beam from the light source 26 has been refracted and is illuminating a point along the photopotentiometer 40. The point on the photopotentiometer 40 on which the light beam falls corresponds to a particular output voltage, which is received by the differential amplifier 61. The reference voltage 62, which may correspond to the photopotentiometer output voltage for either a clear solution or a solution having a fixed known concentration, (e.g., in the middle of the range, such as sg. 1.020), is also received by differential amplifier 62, which measures the difference between its two input voltages and amplifies a signal corresponding to that difference. The amplified signal is received by the voltage-to-frequency convertor 64, which converts amplitude to frequency. This frequency signal is one of the inputs to NAND gate 66.

The second timer 81 measures a period of approximately 40 milliseconds, and sends the second input to NAND gate 66 for that period of time. The NAND gate 66, having both input signals, opens, and the frequency signal is received by the decade counter 67. The decade counter 67 counts each pulse it receives, receiving pulses so long as the NAND gate 66 is open, and passes on a signal which corresponds to that number of pulses to the decoder driver 68. The decoder driver 68 then causes a reading which corresponds to the specific gravity, concentration of dissolved solids, or refractive index of the test sample to be shown at display means 51.

At the end of its cycle, the second timer 81 triggers the third timer 82. The third timer 82 sends a signal through the switch 83 to the transistor 84, the signal of which actuates the solenoid 85 for the drain valve 24, causing it to open thereby draining the hollow prism 13 of any sample. The third timer 82 then also actuates the latch 73 to turn off the red "wait" light 54 and turn on the green "ready" light 53. At the end of the period of the third timer 82, its signal is turned off and solenoid controlled drain valve 24 closes.

Other electronic means such as a suitably programmed microprocessor may serve to perform many or all of the conversion and control functions of the electronic circuitry described herein. Recent advances in microprocessor technology include the integration of analog-to-digital converters and display driver circuitry along with the central processing unit, memory, etc. on a single chip. Such a device may cost effectively implement the design of the present invention, so that the complete invention may be very economically produced.

To those skilled in the art to which this invention relates many changes in construction and widely differing embodiments and applications of the invention will suggest themselves without departing from the spirit and scope of the invention. The disclosures and the descriptions herein are purely illustrative and are not intended to be in any sense limiting.

We claim:

1. A method for determining the concentration of dissolved solids in a liquid sample, comprising the steps of:

directing a collimated beam of monochromatic light through a hollow, empty prismatic container which is enclosed in an opaque housing, detecting the refraction of said beam on its path of emergence from said prismatic container, introducing a liquid sample to be tested into said prismatic container thereby changing the degree of refraction of said beam, disabling measurement of said refraction and further proceeding with the method until after an amount of said liquid sample sufficient for accurate testing has been placed in the prismatic container, and only then, as soon as a predetermined amount of said liquid sample sufficient for accurate testing has been placed in the prismatic container, measuring the refraction of the beam through the sample-filled prism, and displaying of the measured refraction as a function of the concentration of dissolved solids in the sample.

2. The method of claim 1 adapted for testing a series of different liquid samples in which there is a step of automatically draining the sample from the prismatic container upon completion of said measuring step, and repeating the steps of the method for each new sample to be tested.

3. The method of claim 2 in which there is a step of indicating when the container has been drained and is ready to receive another sample.

4. A method for determining the concentration of dissolved solids in a liquid sample, comprising the steps of:

directing a collimated beam of monochromatic light through a hollow, empty prismatic container which is enclosed in an opaque housing, detecting the refraction of said beam on its path of emergence from said prismatic container, introducing a liquid sample to be tested into said prismatic container thereby changing the degree of refraction of said beam, disabling measurement of said refraction and further proceeding with the method until after an amount of said liquid sample sufficient for accurate testing has been placed in the prismatic container, deferring and disabling the measuring step even after the predetermined amount is in the container for a period to free the liquid in the container from air bubbles, and only then, as soon as a predetermined amount of said liquid sample sufficient for accurate testing has been placed in the prismatic container and after said predetermined amount of said liqued sample has had time to be freed from air bubbles, measuring the refraction of the beam through the sample-filled prism, and displaying of the measured refraction as a function of the concentration of dissolved solids in the sample.

5. A method of using a refractometer for determining the amount of dissolved solids in a series of sample solutions which comprises:

directing a collimated monochromatic light beam through an empty hollow prismatic container and refracting it onto first light sensing means, indicating when the refractometer is ready to receive a sample, introducing a sample solution into the prismatic container, thereby causing refraction of the collimated light beam passing therethrough to a second light-sensing means, instead of to the first light-sensing means, commencing the testing sequence only after all of the light beam has been refracted away from the first light-sensing means, and simultaneously indicating that testing is in progress, determining the amount of refraction of the light beam caused by passing through the sample solution, converting the amount of refraction of the light beam into an analog electrical signal, converting the analog signal to a digital signal, displaying digitally an amount corresponding to the digital signal, stated as a function of the concentration of dissolved solids in the sample solution, automatically draining the prismatic container, and simultaneously causing the light beam to be refracted to the first light-sensing means, and automatically recommencing the sequence by indicating that the refractometer is ready to receive another sample.

6. A method of determining the presence of sufficient sample and actuating testing in a refractometer, which comprises:

directing a collimated monochromatic light beam through a desired level of a hollow prismatic container and illuminating a light-sensing means on the opposite side of the prismatic container, delivering a liquid sample to the prismatic container, to refract away from the light-sensing means whichever portion of the light beam passes through the liquid sample, commencing testing when said light-sensing means is no longer illuminated.

7. A refractometer for determining the concentration of dissolved solids in a sample solution, including in combination:

an enclosing opaque housing, light source means in said housing for producing a beam of substantially collimated monochromatic light, a hollow triangular prismatic container in said housing having two transparent optical walls disposed in the path of said light beam and meeting at an angle between about 40° and about 55°, and a third wall, an inlet opening located near the top of the prism, an overflow opening in said third wall located a desired distance below said inlet opening, and a drain opening located at the lower end of said prism, said prismatic container also having a bottom sloping downwardly from said third vertical wall toward the intersection of said two transparent optical vertical walls, and wherein said drain opening is located at substantially the lowermost point of said bottom, light-sensing means disposed in the refracted path of said light beam after the said beam has passed through said prismatic container when filled with a liquid sample and responsive to the exact refraction of said light beam, display means actuated by said light-sensing means for displaying the refraction as a function of the concentration of dissolved solids in the liquid sample, control means to open said drain means and to cause said prismatic container to be emptied after testing has been completed, and indicator means to indicate that the refractometer is ready for the introduction of a new sample.

8. The refractometer of claim 7 wherein said drain means comprises:

a drain opening located at the lower end of said prism, a drain tube connected to said drain opening, a solenoid drain valve having inlet and outlet sides, the inlet side connected to said drain tube, and a waste tube connected to the outlet side of said solenoid drain valve and leading to waste disposing means.

9. A refractometer for determining the concentration of dissolved solids in a sample solution, including in combination:

an enclosing opaque housing, light source means in said housing for producing a beam of collimated monochromatic light, a hollow prismatic container in said housing having two transparent optical vertical walls disposed in the path of said light beam, first and second light-sensing means, said first light-sensing means being disposed in the path of said light beams after the said beam has passed through said prismatic container when empty, and said second light-sensing means being disposed in the refracted path of said light beam after the said beam has passed through said prismatic container when filled with a liquid sample, said second light-sensing means including means responsive to the exact refraction of said light beam, control means to actuate testing as soon as said first light-sensing means ceases being illuminated by said light beam, and differentiating means and display means for comparing the exact refraction of said light beam through a sample to the exact refraction of said light beam through a reference sample and displaying that difference as a function of the concentration of dissolved solids in the test sample.

10. The refractometer of claim 9 wherein said first light-sensing means is a phototransistor and said second light sensing means is a photopotentiometer.

11. The refractometer of claim 9 wherein said first light-sensing means is a phototransistor which emits a signal upon being illuminated, and said control means to actuate testing is an electronic circuit comprising:
an amplifier, connected to said phototransistor,
a Schmitt trigger, connected to said amplifier, and
a timer, connected to said Schmitt trigger via a switch,
the signal of said phototransistor being amplified by said amplifier and received by said Schmitt trigger, so that when said phototransistor ceases being illuminated said Schmitt trigger is operated making a sharp cutoff in the electronic circuit which actuates said timer through said switch.

12. The refractometer of claim 9 wherein said second light-sensing means is a photopotentiometer emitting an output voltage which corresponds to the exact refraction of said light beam as caused by passing through a liquid sample, and said differentiating means is an electronic circuit comprising:
a differential amplifier, said differential amplifier being connected to the output voltage of said photopotentiometer and amplifying an analog signal which corresponds to the difference between said output voltage and the output voltage of a liquid sample having a fixed predetermined concentration of dissolved solids,
an analog-to-digital converter connected to said differential amplifier, receiving said amplifier analog signal, and converting it to a digital signal of pulses at a frequency which corresponds to said amplified analog signal,
a testing duration timer,
a gate connected to and receiving the digital signal of pulses from said analog-to-digital converter, said gate also being connected to said testing duration timer to receive its output during its period, and
a decade counter connected to the output of said gate, so that the digital signal of pulses passes through said gate to be counted by said decade counter only when the output of said timer is also received by the gate, the number of pulses counted by said decade counter being proportional to the concentration of dissolved solids in a test sample.

13. The refractometer of claim 12 having calibrating means for adjusting said differentiating means by setting the period of said timer.

14. The refractometer of claim 13 wherein said calibrating means is an electronic circuit comprising:
first switch means,
an astable timer connected through said first switch means to said control means to actuate testing, said astable timer also being connected to said decade counter to reset said decade counter at the beginning of each period of said astable timer,
second switch means connecting the output of said astable timer to actuate and re-actuate said testing duration timer at the beginning of each period of said astable timer, and
adjustment means connected to said testing duration timer, said adjustment means controlling the period for which said testing duration timer is set.

15. The refractometer of claim 12 wherein the period of said timer is approximately 40 milliseconds.

16. The refractometer of claim 9 wherein said hollow prismatic container is triangular, having a third wall, an inlet opening located near the top of the prism, and overflow opening in said third vertical wall located a desired distance below said inlet opening, and a drain opening located at the lower end of said prism.

17. The refractometer of claim 16 wherein said hollow prismatic container has a bottom sloping downwardly from said third wall toward the intersection of said two transparent optical walls, and wherein said drain opening is located at substantially the lowermost point of said bottom.

18. The refractometer of claim 16 wherein said hollow prismatic container is a triangle in which the two transparent walls meet at an angle of between about 40° and about 55°.

19. The refractometer of claim 9 having control means, and drain means connected to said hollow prismatic container, said control means to open said drain means causing said prismatic container to be emptied after testing has been completed.

20. The refractometer of claim 19 wherein said drain means comprises:
a drain opening located at the lower end of said prism,
a drain tube connected to said drain opening,
a solenoid drain valve having inlet and outlet sides, the inlet side connected to said drain tube, and
a waste tube connected to the outlet side of said solenoid drain valve and leading to waste disposing means.

21. The refractometer of claim 9 having calibrating means for adjusting said differentiating means.

22. A refractometer for determining the concentration of dissolved solids in a sample solution, including in combination:
an enclosing opaque housing,
light source means in said housing for producing a beam of substantially collimated monochromatic light,
a hollow prismatic container in said housing, said prismatic container being triangular, having two transparent optical vertical walls disposed in the path of said light beam, a third vertical wall, an inlet opening located near the top of said prism, and overflow opening disposed in said third vertical wall at a desired distance from the top of said prism, a bottom sloping downwardly from said third vertical wall toward the intersection of said two transparent optical vertical walls, and a drain opening located at substantially the lowermost point of said bottom,
a phototransistor which emits a signal upon being illuminated, said phototransistor being disposed in the path of said light beam after the said beam has passed through said prismatic container while empty,
an amplifier connected to said phototransistor, a Schmitt trigger connected to said amplifier, and a first timer connected to said Schmitt trigger via a first switch, the signal of said phototransistor being amplified by said amplifier and received by said Schmitt trigger so that when said phototransistor ceases being illuminated, said Schmitt trigger is operated making a sharp cutoff in the electronic circuit actuating said timer through said first switch, a photopotentiometer, said photopotentiometer being disposed in the refracted path of said light beam after the said beam has passed through said prismatic container while filled with a liquid sample, said photopotentiometer emitting an output voltage which corresponds to the exact refraction of said beam as caused by passing through a liquid sample, a differential amplifier, said differential amplifier being connected to the output voltage of said photopotentiometer to amplify an analog signal which corresponds to the difference between said output voltage and the output voltage of a liquid sample having a fixed known concentration of dissolved solids, an analog-to-digital converter connected to said differential amplifier, to receive said amplified analog signal and converting it to a digital signal of pulses at a frequency which corresponds to the said amplified analog signal, a second timer connected to the output of said first timer to be actuated at the end of its period, a gate connected to said second timer, and a decade counter connected to the output of said gate, said gate being connected to and receiving the digital signal of pulses from said analog-to-digital converter, said gate being connected to said second timer to receive its output during its period, the digital signal of pulses passing through said gate to be counted by said decade counter only when the output of said timer is also received by the gate, the number of pulses counted by said decade counter corresponding to the concentration of dissolved solids in a test sample, display means for displaying a digital figure which corresponds to the concentration of dissolved solids in a test sample, said display means being connected to the output of said decade counter through a decoder driver, a drain tube connected to the drain opening in said prismatic container, a solenoid drain valve having inlet and outlet sides, the inlet side connected to said drain tube, and a waste tube connected to the outlet side of said solenoid drain valve, leading to waste-disposing means, a third timer, said third timer being connected to said second timer to be actuated upon the completion of testing, said third timer to emit a signal upon being actuated, switch means connected to receive the signal from said third timer, transistor means connected to said switch means to receive the signal from said third timer means, an amplifier connected to said transistor means to receive and amplify its signal, said amplified signal actuating the opening of said solenoid drain valve for the period of said third timer, and warning means to indicate that the refractometer is ready for the introduction of a new sample.

* * * * *

UNITED STATES PATENT AND TRADEMARK OFFICE
CERTIFICATE OF CORRECTION

PATENT NO. : 4,381,895
DATED : May 3, 1983
INVENTOR(S) : Leonard A. Hughes, Evan R. Flavell and Benjamin C. Willman It is certified that error appears in the above-identified patent and that said Letters Patent are hereby corrected as shown below:

Column 4, line 4, "outlet opening" should read

--inlet opening--.

Column 11, line 39, which is line 15 of claim 12,

"amplifier analog" should read --amplified analog--.

Signed and Sealed this

Ninth Day of August 1983

[SEAL]

Attest:

GERALD J. MOSSINGHOFF

Attesting Officer

Commissioner of Patents and Trademarks